(12) United States Patent
Klunder et al.

(10) Patent No.: US 9,176,062 B2
(45) Date of Patent: Nov. 3, 2015

(54) APERTURE BIOSENSOR WITH TRENCHES

(75) Inventors: Derk J. W. Klunder, Eindhoven (NL);
Maarten M. J. W. Van Herpen,
Eindhoven (NL); Hendrik R. Stapert,
Eindhoven (NL)

(73) Assignee: Koninklijke Philips N.V., Eindhoven (NL)

(*) Notice: Subject to any disclaimer, the term of this patent is extended or adjusted under 35 U.S.C. 154(b) by 986 days.

(21) Appl. No.: 12/519,849

(22) PCT Filed: Dec. 17, 2007

(86) PCT No.: PCT/IB2007/055159
§ 371 (c)(1),
(2), (4) Date: Jun. 18, 2009

(87) PCT Pub. No.: WO2008/078263
PCT Pub. Date: Jul. 3, 2008

(65) Prior Publication Data
US 2010/0001210 A1     Jan. 7, 2010

(30) Foreign Application Priority Data
Dec. 21, 2006  (EP) .................................. 06126771

(51) Int. Cl.
*G01N 27/00*     (2006.01)
*G01N 21/64*     (2006.01)

(52) U.S. Cl.
CPC .................................. *G01N 21/648* (2013.01)

(58) Field of Classification Search
CPC .................. B01L 2300/0816; B01L 2200/025;
B01L 2300/0654; B01L 2300/0887; B01L
3/502715; B01L 3/50273; B01L 3/502761;
G01N 21/554; G01N 21/648; G01N 21/658;
G01N 2021/95676; G01N 21/47; C12Q
1/6837

USPC ............. 422/82.01, 82.05, 82.07, 8.08, 82.11
See application file for complete search history.

(56) References Cited

U.S. PATENT DOCUMENTS

| 2002/0034457 A1 | 3/2002 | Reichert et al. |
| 2003/0174992 A1 | 9/2003 | Levene et al. |

(Continued)

FOREIGN PATENT DOCUMENTS

| JP | 2007198801 | 8/2007 |
| WO | 9320240 A1 | 10/1993 |
| WO | 0009757 A1 | 2/2000 |

(Continued)

OTHER PUBLICATIONS

Foquet et al, Substrates for Performing Analytical Reactions, Jun. 12, 2006,U.S. Appl. No. 60/812863, Entire Document.*
Weiss, S.: "Fluorescence Spectroscopy of Single Biomolecules"; Science, vol. 283, No. 5408, pp. 1676-1683, Mar. 12, 1999.

*Primary Examiner* — Dennis M White

(57) ABSTRACT

A luminescence sensor, comprising a non-transparent substrate structure (2) having at least one aperture (5) intended to comprise an analyte and a transparent substrate structure (3), which is arranged to or adjacent said first structure (2). The aperture has a smallest lateral dimension, which is smaller than half the effective wavelength of an excitation radiation, such as light at a wavelength of 700 nm, resulting in an effective wavelength in water of about 538 nm. The transparent structure has a trench (4) with a surface portion provided with ligands with an affinity towards a target molecule. The trench results in that a luminophore attached to the target molecule will be positioned at the entrance surface of the aperture, where the excitation energy is largest.

16 Claims, 2 Drawing Sheets

(56) References Cited

U.S. PATENT DOCUMENTS

2003/0215872 A1 11/2003 Clark
2004/0113095 A1 6/2004 Peltie et al.
2004/0200979 A1 10/2004 Reel
2007/0134128 A1* 6/2007 Korlach ......................... 422/56

FOREIGN PATENT DOCUMENTS

| WO | 2006033914 A2 | 3/2006 |
| WO | 2006136991 A1 | 12/2006 |
| WO | 2007072293 A2 | 6/2007 |
| WO | 2007149724 A2 | 12/2007 |

* cited by examiner

APERTURE BIOSENSOR WITH TRENCHES

FIELD OF INVENTION

The present invention relates to the field of biosensors and more specifically to sub-wavelength sensors, namely sub-diffraction limited sensors.

BACKGROUND OF THE INVENTION

Biosensor technology is well known in the art.

US Patent Application No. 2003/0174992 discloses a method and an apparatus for providing a zero-mode waveguide including an analyte, which is subjected to activation by electromagnetic radiation for analyzing the analyte.

European Patent Application No. 05105599.4, entitled "Luminescence sensors using sub-wavelength apertures or slits", filed on Jun. 23, 2005, discloses a biosensor with sub-wavelength spatial resolution operating inside a fluid.

In such a biosensor, an analyte may be arranged in apertures having at least partly sub-wavelength dimensions. The analyte may be included in a fluid. A luminophore present in the fluid emits radiation when exposed to excitation energy. The emitted radiation is collected by a detector.

A disadvantage of these type of biosensors is that the luminescent energy originating from an individual luminophore may depend on the position of the luminophore inside the aperture. As a result, these type of biosensors may have a response that has a poor quantitative relationship to the analyte to be analyzed, resulting in a poor accuracy of the detected property.

SUMMARY OF THE INVENTION

Accordingly, an object of the present invention is to mitigate, alleviate or eliminate one or more of the above-identified deficiencies and disadvantages singly or in any combination.

According to an aspect of the invention, there is provided a substrate to be included in a sensor, preferably a luminescence sensor, comprising: a non-transparent substrate structure having at least one aperture for comprising an analyte; a transparent substrate structure, which is arranged to or adjacent said first structure and has a surface portion with a binding capacity in relation to said analyte; said surface portion being arranged at a predetermined distance from one end of said aperture.

In an embodiment, the surface portion may be arranged at a predetermined distance outside the end of said aperture. The surface portion may comprise at least one ligand having an affinity towards target molecules included in the analyte. The distance may be approximately equal to the average of a ligand length.

In another embodiment, the distance is equal to the sum of the ligand length, the target molecule size and a constant length. The constant length may be 1 to 50 nm, such as 1 to 10 nm.

In a further embodiment, the distance may be 1 to 60 nm, such as 3 to 25 nm. Alternatively, the distance may be 1 to 15 nm. The distance may be 60 to 1000 nm.

In a yet another embodiment, the surface is arranged in a trench formed in said transparent structure. The trench may have a dimension corresponding to the aperture and may be arranged opposite the aperture.

In a yet further embodiment, the aperture may have at least one lateral dimension which is below the diffraction limit or less than 50% of an effective wave-length of a luminescence radiation or an excitation radiation for a luminophore included in said analyte. The aperture may have a first lateral dimension that is less than the diffraction limit or 50% of an effective wavelength and a second lateral dimension above the diffraction limit or larger than 50% of an effective wavelength. Alternatively, the aperture may be substantially circular, elliptical.

According to the invention, it is further proposed a sensor substrate for a luminescence sensor and a luminescence sensor comprising this sensor substrate.

BRIEF DESCRIPTION OF THE DRAWINGS

Further objects, features and advantages of the invention will become apparent from the following detailed description of embodiments of the invention with reference to the drawings, in which.

DETAILED DESCRIPTION OF EMBODIMENTS

Figure 1:
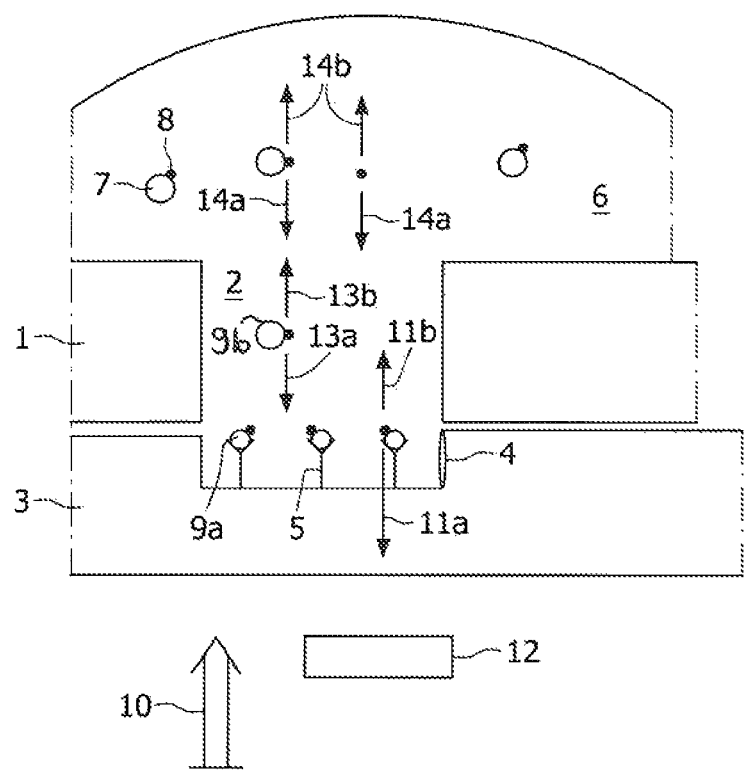
FIG. 1 is a schematic illustration of a first and second embodiment of a biosensor.

Below, several embodiments of the invention will be described with references to the drawings. These embodiments are described in illustrating purpose in order to enable a skilled person to carry out the invention and to disclose the best mode. However, such embodiments do not limit the invention. Moreover, other combinations of the different features are possible within the scope of the invention.

A biosensor substrate according to the embodiments described below may comprise an analyte arranged in apertures of a first type having both lateral in-plane dimension below the diffraction limit of the used excitation light in the medium that fills the aperture. In other embodiments, the apertures are of a second type having a first lateral in-plane dimension below the diffraction limit in the medium that fills the apertures and a second lateral in-plane dimension above the diffraction limit in the medium that fills the apertures. By in-plane dimension is meant the dimension in a plane parallel to the substrate.

Due to the sub-diffraction-limited dimensions in at least one in-plane dimension of the aperture, the excitation radiation penetrates into the apertures, but the transmission of the aperture is small and as a result the excitation energy behind the apertures is substantially suppressed. For apertures of the first-type this is the case for all polarizations of the light, while for apertures of the second-type this is only the case for R-polarized light. R-polarized light is defined as light with an electric field in a direction normal to the transmission plane of the aperture, which is a plane normal to the substrate and parallel with a vector along the first dimension of the aperture. The detected luminescent energy originates, thus, essentially only from luminophores inside the apertures and a small number of luminophores inside the apertures can be distinguished from the often large number of luminophores outside and behind the aperture.

The analyte may be included in a fluid. A luminophore present in the fluid emits electromagnetic radiation when exposed to excitation energy. The emitted radiation is collected by a detector.

The total radiation energy, i.e. the sum of the radiation energy of the individual luminophores emitted by the luminophores, has a predetermined relationship to a property of the analyte such as being proportional to a concentration of a target molecule of the analyte. By analyzing the emitted radiation, the property of the analyte can be determined, quantitatively and/or qualitatively.

The radiation emitted by the luminophore can be detected at either side of the biosensor substrate. If the analyte fluid is present on one side, the radiation can be detected at the other side. In this case, as a result of the substantial suppression of the excitation light by the aperture, the radiation emitted by a luminophore present in the fluid outside the apertures is significantly smaller than the radiation emitted by a luminophore present close to the entrance portion of the aperture, where the excitation light is not attenuated. Thus, the detected radiation is essentially only radiation emitted by luminophores present close to the entrance portion of the apertures. Hence, a high signal-to-background and signal-to-noise ratio can be obtained since the background radiation may be reduced.

Ligands or capture molecules may be arranged or immobilized at specific portions of the aperture. The said ligands or capture molecules may have an affinity towards target molecules, such that target molecules can bind specifically with the said ligands or capture molecules. As a result the target molecules may bind specifically at said specific portions of the aperture. The target molecules may be a luminescent molecule, or may be labeled with a luminescent molecule. The thus-formed aggregate of ligands or capture molecules and target molecules forms a luminophore. In the context of the present invention, a luminiphore refers to a particle, bead, molecule or aggregate of molecules, or particles, or beads that is capable of emitting luminescent radiation. Such formation of luminophores may take place in different manners, such as described in the article: "Fluorescence spectroscopy of single biomolecules" by S. Weiss, Science, Vol. 283, pp 1676-1683, the technical contents of which are hereby incorporated by reference. In the context of the present invention luminophore also refers to a luminescently labeled molecule The ligands may immobilize the luminophores so that they emit radiation from the immobilized positions at excitation. As a first example consider ligands such oligonucleotides, which bind specifically to nucleic acids having a complementary sequence (the target molecules), immobilized at specific portions of the aperture. For deoxyoligonucleotides (DNA), a polymerase chain reaction is often used to amplify the DNA concentration, and fluorescent labeling of the resulting target molecules (amplicons). A fragment of the sequence of the amplicons is complementary with and can bind to (hybridize with) the oligonucleotides immobilized at specific portions of the aperture. As a second example consider a sandwich assay were antibodies specific for the target protein are immobilized at specific portions of the aperture. First the targeted protein molecule binds to the antibody, where after fluorescently labeled antibodies present in the analyte containing fluid bind to the targeted protein molecule. Both examples result in fluorescently labeled aggregates immobilized at specific portions of the aperture.

Depending on the position along the aperture, the excitation light and emitted radiation will be attenuated by the aperture in different degrees. This may result in that radiation from luminophores present inside the aperture at the exit side will give a smaller response from the detector compared to the luminophores close to the entrance side. Thus, if luminophores are present all over the aperture, the detector response will not be proportional to the number of luminophores present in the aperture, while luminophores present closer to the entrance portion will contribute more to the detector signal than luminophores present inside the aperture. The substrate structure wherein the apertures are defined may be partly or completely composed of a metal, such as aluminum, gold, silver, chromium, etc. Luminophores such as fluorophores close (typically less than 10 nm) to a metal can couple their fluorescence to a metal via near field interaction resulting in quenching of the fluorescence. As a result the luminescent power for a luminophore close to the metal of the apertures is different than the luminescent power further away from the metal.

The luminophores may be excited to emit radiation in different manners, such as by electric or chemical energy. The emitted radiation may take place by different physical processes, such as luminescence, phosphorescence, fluorescence, Raman scattered light, Hyper-Raman scattered light or Hyper-Rayleight scattered light etc. The emitted radiation may be electromagnetic radiation, such as light, including infrared light.

Below, excitation with electromagnetic radiation will be considered, specifically light, including infrared light, with a wavelength in the relevant medium that is larger than at least one lateral dimension of the aperture. The effective wavelength is the wavelength of the radiation in vacuum divided by the refractive index of the medium.

If at least one lateral dimension of the aperture is smaller than half the effective wavelength in the medium that fills the aperture then an evanescent electromagnetic field will be established in the aperture. For an aperture with one lateral dimension larger than half the effective wavelength, an evanescent electromagnetic field also involves R-polarized light.

Such an evanescent field may excite the luminophores present in the aperture. The evanescent field will have an exponential decay in the aperture from the entrance side or facet of the aperture. Thus, luminophores present close to the inlet side will be more efficiently excited than luminophores present inside the aperture and beyond the aperture at the other side of the aperture.

In an embodiment, the exit side of the radiation emitted by the luminophores is the same as the inlet side of the excitation radiation. In this case the reduced excitation efficiency along the aperture length (which is in a direction normal to a plane that is parallel to the substrate) will add to the attenuation by the aperture of the radiation emitted by the luminophores if the luminophore is present or immobilized inside the aperture at a distance from the inlet/emit side of the aperture.

Moreover, excitation radiation will pass through the aperture, although attenuated by the aperture, a typical value for this attenuation is a factor 1000, and exit at the other side of the aperture. Such passing radiation will excite luminophores present in the medium and form background radiation. Such radiation will pass through the apertures in the form of background radiation and add to the signal in the detector. If the useful signal is lowered, as explained above, the signal-to-background and also the signal-to-noise ratio will be lowered.

If the luminophores are immobilized by a ligand as explained above, the ligand may be attached to a surface at the exit portion of the aperture. However, the ligand has a certain length, which may be for example 1 to 60 nm. Since the length of the aperture may be in the region of 50 to 1000 nm, such ligand length will result in that the luminophores are positioned a substantial distance inside the aperture or in some cases even outside the aperture. Since the excitation energy decays exponentially, the positioning of the ligands inside the aperture will result in that the luminophores are exposed to less excitation energy and, thus, emit less radiation towards the detector. Moreover, the emitted light passes along the aperture and becomes attenuated to a certain degree, also contributing to a decreased of the useful signal. Since the background radiation is unaltered, the decrease of the useful signal results in a reduced signal-to-background and signal-to-noise ratio.

A ligand immobilized at a surface may have less affinity towards a target molecule if the ligand is positioned close to the surface. Thus, the ligand may comprise a spacer, further increasing the total ligand length.

FIG. 1 discloses a biosensor substrate according to the prior art. The biosensor substrate comprises a substrate structure 1. The substrate structure is substantially opaque or non-transparent for the relevant radiation, such as light at a wavelength (in vacuum) of about 700 nm. The substrate structure may be partly or completely composed of a metal, such as gold; aluminum; silver; chromium, etc. The material where the substrate structure is partly or completely composed of should have a refractive index having a substantial imaginary component. The said imaginary component of the refractive index, is preferably larger than 1, more preferably larger than 3 and most preferably larger than 6.

The substrate structure 1 comprises at least one aperture 2 having a first in-plane lateral dimension smaller than 50% of an effective wavelength of the medium for filling the aperture. Several apertures may be arranged at the surface of the substrate 1, such as with regularly spaced intervals. The apertures may be grouped as disclosed in US Patent Application No. 2003/0174992.

The aperture may have any shape, such as circular, elliptic, triangular, rectangular, hexagonal, etc. The aperture may be arranged as a slit having a first in-plane lateral dimension smaller than 50% of an effective wavelength of the medium for filling the aperture and a second in-plane lateral dimension larger than 50% of an effective wavelength of the medium for filling the aperture. The aperture may be arranged as a combination of two slit arrangements as disclosed in European Patent Application No. 05198773.2 filed Sep. 22, 2005.

The first in-plane lateral dimension may be smaller than 40%, more preferably between 15% and 25%, and most preferably between 10% and 15% of an effective wavelength in the medium for filling the aperture. For an aperture of the second type, the second in-plane lateral dimension may be between 1 and 10 times, more preferably between 10 and 200 times, and most preferably more than 200 times an effective wavelength in the medium for filling the aperture. The wavelength of the excitation light may be around 633 nm, with water (index of refraction 1.33) as a medium for filling the aperture, corresponding with an effective wavelength of 476 nm. The first in-plane lateral dimension may be smaller than 190 nm, more preferably between 71 nm and 119 nm, and most preferably between 48 nm and 71 nm. For an aperture of the second type, the second in-plane lateral dimension may be between 0.48 μm and 5 μm, more preferably between 5 μm and 100 μm, and most preferably more than 100 μm. Alternatively, the wavelength of the excitation light may be around 350 nm, with water (index of refraction 1.35) as a medium for filling the aperture, corresponding with an effective wavelength of 260 nm. The first in-plane lateral dimension may be smaller than 103 nm, more preferably between 39 nm and 65 nm, and most preferably between 26 nm and 391 nm. For an aperture of the second type, the second in-plane lateral dimension may be between 0.26 μm and 2.5 μm, more preferably between 2.5 μm and 50 μm, and most preferably more than 50 μm.

A transparent structure 3 is arranged below the substrate structure 1 supporting the substrate structure. The transparent structure 3 is made of a material that is substantially transparent to the excitation and may also be transparent to the emitted radiation. The material may be glass, acrylic glass, epoxy resin, polyvinylchloride (PVC), etc In order to be sufficiently transparent, the material should have a refractive index with an imaginary part smaller than $10^{-4}$.

A surface of the transparent structure 3 forms a bottom of the apertures 2 as shown in FIG. 1. The surface is provided with a recess or trench 4 coinciding with the aperture 2. The trenches are made by etching the transparent material opposite to the apertures. Other methods of forming the trenches may be to add distance members to the transparent material at regular intervals.

The surface in the trench 4 is surface modified to include capture molecules such as ligands 5. The ligands 5 have an affinity towards target molecules 7 present in a fluid 6, which is present in the aperture 2 and above the substrate 1. The target molecules 7 are labeled with a luminophore 8.

A luminophore is a molecule or particle that generates luminescent radiation when exposed for energy from an excitation source. A fluorophore is a molecule or particle that generates electromagnetic radiation, such as light or infrared light by fluorescence when exposed for energy from a light source, including infrared light. Whenever there is referred to fluorescence or a fluorophore in this specification, it can alternatively be intended to mean luminescence or a luminophore.

The operation of the embodiment of FIG. 1 is as follows. Target molecules 7 having a fluorophore 8 attached thereto enters the aperture 2 and are caught by ligands 5 immobilized on the surface of the trench 4. Three such aggregates 9 of a ligand 5, a target molecule 7 and a fluorophore 8 are shown in the trench in FIG. 1. The fluid is substantially water having a refractive index of 1.3.

For an aperture of the first-type, the biosensor substrate is exposed to light 10 from the transparent structure 3 side. The light 10 has a wavelength of 700 nm in vacuum corresponding to an effective wavelength of 538 nm in water. Both lateral in-plane dimensions of the aperture are smaller than about 269 nm, i.e. smaller than 50% of the effective wavelength, such as 70 nm. Thus, an evanescent electromagnetic field is present inside the aperture with exponentially decaying field strength.

For an aperture of the second-type, the biosensor substrate is exposed to R-polarized light 10 from the transparent structure 3 side. The R-polarized light 10 has a wavelength of 700 nm in vacuum corresponding to an effective wavelength of 538 nm in water. The first lateral in-plane dimensions of the aperture is smaller than about 269 nm, i.e. smaller than 50% of the effective wavelength, such as 70 nm. The second lateral in-plane dimension is larger than about 269 nm, i.e. larger than 50% of the effective wavelength, such as 1 mm. Thus, an evanescent electromagnetic field is present inside the aperture with exponentially decaying field strength.

Other wavelength radiation may be used as well such as microwaves, infrared light, near-infrared (NIR) light, visible light, ultraviolet light, X-ray, etc.

A fluorophore present in aggregate 9a present at the surface of the trench 4 is excited and emits radiation as indicated by arrows 11a and 11b. About 50% of such radiation according to arrow 11a is directed towards a detector 12 present below the sandwich member 3. The other 50% of the emitted radiation as indicated by arrow 11b is directed into the aperture and is attenuated therein. Since the fluorophore is excited by non-attenuated excitation light—due to the reflection of the excitation light 10 by the aperture the energy of the excitation light in the trench is actually increased by about a factor 2, and since a large portion of the emitted radiation reaches the detector, a high efficiency is obtained.

A fluorophore attached to a target molecule 7 present inside the aperture as indicated by aggregate 9b is exposed to an excitation radiation, which has been greatly attenuated inside the aperture. Thus, such fluorophore emits less radiation than the fluorophore present in aggregate 9a, because the power of the emitted fluorescence is proportional to the intensity of the—for fluorophore 9b reduced—excitation radiation. The emitted radiation, which is directed towards the detector 12 as indicated by arrow 13a, is attenuated by the action of the aperture, which is also relevant for the radiation directed in the other direction as indicated by arrow 13b.

A small fraction of the excitation radiation reaches outside the aperture into the fluid present above the aperture. In a practical biosensor, the attenuation of such radiation is about 1000 and depends—for given lateral dimensions of the aperture—on the length of the aperture. For an aperture length of 160 nm and first lateral in-plane dimension of 70 nm, the attenuation of the excitation radiation that has passed the aperture is about 1000. Such radiation will excite fluorophores present in the fluid, such as fluorophores labeled to the free target molecules as well as free fluorophores non-attached to a target molecule. Such fluorophores will emit radiation and a fraction thereof, as indicated by arrow 14a will enter the aperture and pass to the detector 12 again attenuated by the aperture. Such radiation 13a and 14a forms background radiation. In addition, exciting radiation reflected back to the detector will add to the background radiation. A wavelength filter that transmits the fluorescent radiation and blocks the excitation radiation may be used to attenuate the reflected excitation radiation.

The background radiation can be reduced by washing away free target molecules and fluorophores. However, such washing may not be possible in real-time measurements. Moreover, some target molecules and fluorophores may stay in spite of such washing.

As shown in FIG. 1, the trench has a certain depth corresponding to the length of the ligand 5 so that the luminophore is present at the exit surface of the aperture. As an example, for a sandwich assay the target molecules are sandwiched between a first acceptor molecules at the binding interface and a second fluorescently labeled acceptor molecule.

The depth may be equal to the length of the ligand. For Sandwich assays it is typically 10 to 60 nm; for peptide-antibody assays it is 3 to 25 nm; for DNA hybridization assays it can be 1 to 15 nm.

Since the excitation energy is approximately constant outside the aperture, the depth of the trench can be slightly larger than the ligand length, such as 1 to 50 nm larger.

The depth may be the sum of the ligand length, the size of the target molecule and a predetermined constant.

A suitable depth is 1 to 60 nm, but a depth up to 1000 nm may be used in certain applications.

If the ligands are not recessed as shown in FIG. 1 but are arranged at the interface between the transparent structure 3 and the non-transparent structure 1, the excitation energy will be substantially attenuated before reaching the fluorophores as explained above. Thus, the detected power of the radiation generated by aggregates 9a may be reduced by a factor of 10 in a practical embodiment, while the detected background radiation remains essentially the same, thus resulting in a reduction of the background suppression.

Figure 2:
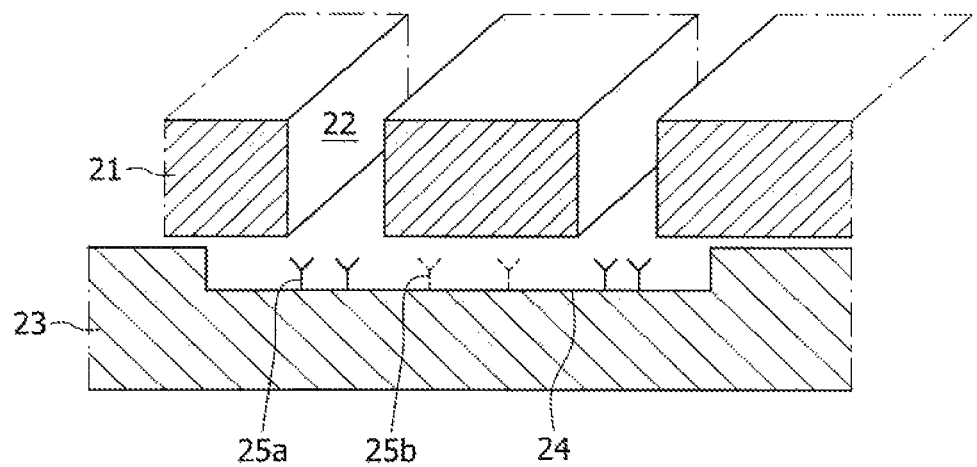
FIG. 2 is a schematic illustration of another embodiment of a biosensor.

FIG. 2 discloses another embodiment, in which at least one of the lateral in-plane dimensions of the trench 24 is made substantially larger than the corresponding, that is parallel to, lateral in-plane dimension of the aperture 22. The trench may be provided by ligands 25a over the surface corresponding to the apertures. Additionally, the trench may be provided with ligands 25b over the surface in between the apertures.

In a further embodiment, ligands are only present opposite to the apertures.

Figure 3:
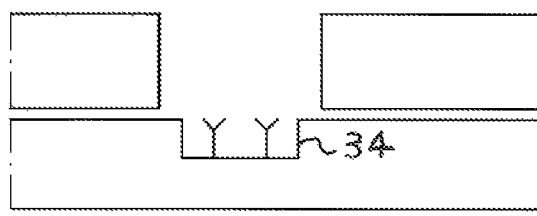
FIG. 3 is a schematic illustration of a further embodiment of a biosensor.

In a still further embodiment, shown in FIG. 3, the trench 34 is only present over a portion of the exit area of the aperture.

The area between the trenches can form structures for supporting the substrate structure comprising the apertures. If the apertures are formed by a wire structure, the trenches may extend over multiple wires and act as support structure for the wires.

The trench surface is provided with ligands, which may take place in any conventional manner. The ligands may be a protein, a peptide, an antibody or a fragment thereof, a sequence specific probe that is complimentary to the targeted DNA sequence, a carbohydrate, a hormone, an antioxidant, a glycoprotein, a lipoprotein, a reactive dye or combinations thereof.

In the above embodiments, the biosensor is operated in reflection mode, wherein the signal is detected at the same side as the excitation radiation is arranged. In this case, the excitation radiation should be prevented from reaching the detector, which may take place by filters, such as polarizing filters or wavelength filters that block the excitation radiation.

The same principle may as well be used in transmission mode with the disadvantage that the generated fluorescent radiation is somewhat suppressed because it has to propagate through the apertures.

Although the present invention has been described above with reference to specific embodiment, it is not intended to be limited to the specific form set forth herein. Rather, the invention is limited only by the accompanying claims and, other embodiments than the specific above are equally possible within the scope of these appended claims.

In the claims, the term "comprises/comprising" does not exclude the presence of other elements or steps. Furthermore, although individually listed, a plurality of means, elements or method steps may be implemented by e.g. a single unit or processor. Additionally, although individual features may be included in different claims, these may possibly advantageously be combined, and the inclusion in different claims does not imply that a combination of features is not feasible and/or advantageous. In addition, singular references do not exclude a plurality. The terms "a", "an", "first", "second" etc do not preclude a plurality. Reference signs in the claims are provided merely as a clarifying example and shall not be construed as limiting the scope of the claims in any way.

The invention claimed is:

1. A sensor substrate, comprising:
   a non-transparent substrate structure having at least one aperture for including analyte;
   a transparent substrate structure arranged adjacent to said non-transparent substrate structure; and
   at least one trench including a surface portion formed in the transparent substrate structure, the surface portion
      coinciding with and forming a bottom of the at least one aperture,
      is arranged at a predetermined distance from said aperture, having a higher binding capacity in relation to said analyte than elsewhere on the transparent substrate, and
      comprising a lateral in-plane dimension different than the corresponding lateral in-plane dimension of the aperture.

2. The sensor substrate according to claim 1, wherein the predetermined distance is outside the end of said aperture.

3. The sensor substrate according to claim 2, wherein said surface portion comprises at least one ligand having a first length and an affinity towards target molecules included in the analyte.

4. The sensor substrate according to claim 3, wherein said distance is approximately equal to the average of the first length.

5. The sensor substrate according to claim 3, wherein said distance is equal to the sum of the first length, a length of the target molecule and a constant length.

6. The sensor substrate according to claim 5, wherein said constant length is 1 to 10 nm.

7. The sensor substrate according to claim 2, wherein said distance is 3 to 25 nm.

8. The sensor substrate according to claim 2, wherein said distance is 1 to 15 nm.

9. The sensor substrate according to claim 2, wherein said distance is 60 to 1000 nm.

10. The sensor substrate according to claim 1, wherein said surface portion is arranged in the trench formed in said transparent structure.

11. The sensor substrate according to claim 1, wherein the trench has a dimension corresponding to the aperture and is arranged opposite the aperture.

12. The sensor substrate according to claim 1, wherein said aperture has at least one lateral dimension which is smaller than 50% of an effective wave-length of an emission radiation for a luminophore included in said analyte, wherein the effective wavelength is the wavelength of the emission radiation in a vacuum divided by a refractive index of the analyte medium.

13. The sensor substrate according to claim 12, wherein said aperture is a slit having a second in-plane dimension which is larger than 50% of an effective wavelength of an excitation radiation.

14. The sensor substrate according to claim 12, wherein the length of the aperture is between 0.5 to 10 times said lateral dimension.

15. The sensor substrate according to claim 1, wherein the sensor comprises a luminescence sensor.

16. The sensor substrate according to claim 1, wherein the at least one aperture reflects excitation light and energy of the excitation light in the trench is increased by about a factor 2.

* * * * *